(12) United States Patent
Dubrow et al.

(10) Patent No.: US 6,475,364 B1
(45) Date of Patent: Nov. 5, 2002

(54) METHODS, DEVICES AND SYSTEMS FOR CHARACTERIZING PROTEINS

(75) Inventors: Robert S. Dubrow, San Carlos, CA (US); Christopher Bloxsom, Palo Alto, CA (US); Calvin Y. H. Chow, Portola Valley, CA (US); J. Wallace Parce, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/496,849

(22) Filed: Feb. 2, 2000

Related U.S. Application Data

(63) Continuation-in-part of application No. 09/243,149, filed on Feb. 2, 1999, now abandoned.

(51) Int. Cl.[7] .................. G01N 27/26; G01N 15/06; G01N 27/453; G01N 27/447
(52) U.S. Cl. .................. 204/455; 204/451; 204/601; 204/605; 422/68.1; 422/100
(58) Field of Search ................ 422/68.1, 99, 100; 204/514, 455, 601, 605

(56) References Cited

U.S. PATENT DOCUMENTS

| | | |
|---|---|---|
| 4,077,845 A | 3/1978 | Johnson |
| 4,390,403 A | 6/1983 | Batchelder |
| 4,908,112 A | 3/1990 | Pace |
| 4,963,498 A | 10/1990 | Hillman |
| 5,015,350 A | 5/1991 | Wiktorowicz |
| 5,089,111 A | 2/1992 | Zhu et al. |
| 5,110,424 A | 5/1992 | Chin |
| 5,126,021 A | 6/1992 | Grossman |
| 5,126,022 A | 6/1992 | Soane et al. |
| 5,140,161 A | 8/1992 | Hillman |
| 5,144,139 A | 9/1992 | Hillman |
| 5,164,598 A | 11/1992 | Hillman |
| 5,171,534 A | 12/1992 | Smith et al. |
| 5,181,999 A | 1/1993 | Wiktorowicz |
| 5,264,101 A | 11/1993 | Demorest et al. |

(List continued on next page.)

FOREIGN PATENT DOCUMENTS

| | | |
|---|---|---|
| EP | 665 430 A1 | 8/1995 |
| WO | WO 9604547 | 2/1996 |
| WO | WO 9702357 | 1/1997 |

OTHER PUBLICATIONS

Yao, S. et al., "SDS capillary gel electrohoresis of proteins in microfabricated channels," *PNAS* (May 1999) 96:5372–5377.

(List continued on next page.)

*Primary Examiner*—Jill Warden
*Assistant Examiner*—Alex Noguerola
(74) *Attorney, Agent, or Firm*—Matthew B. Murphy; Gulshan H. Shaver

(57) ABSTRACT

A method of characterizing a polypeptide, comprising providing a first capillary channel having a separation buffer disposed within, wherein the separation buffer comprises a non-crosslinked polymer solution, a buffering agent, a detergent, and a lipophilic dye. The separation buffer is provided such that, at the time of detection, the detergent concentration in the buffer is not above the critical micelle concentration. The polypeptide is introduced into one end of the capillary channel. An electric field is applied across a length of the capillary channel, which transports polypeptides of different sizes through the polymer solution at different rates. The polypeptide is then detected as it passes a point along the length of the capillary channel.

32 Claims, 11 Drawing Sheets

U.S. PATENT DOCUMENTS

| | | | |
|---|---|---|---|
| 5,332,481 | A | 7/1994 | Guttman |
| 5,374,527 | A | 12/1994 | Grossman |
| 5,498,392 | A | 3/1996 | Wilding et al. |
| 5,500,071 | A | 3/1996 | Kaltenbach |
| 5,552,028 | A | 9/1996 | Madabhushi et al. |
| 5,560,811 | A | 10/1996 | Briggs |
| 5,567,292 | A | 10/1996 | Madabhushi et al. |
| 5,571,410 | A | 11/1996 | Swedberg et al. |
| 5,585,069 | A | 12/1996 | Zanzucchi et al. |
| 5,593,838 | A | 1/1997 | Zanzucchi et al. |
| 5,599,432 | A | 2/1997 | Manz et al. |
| 5,603,351 | A | 2/1997 | Cherukuri et al. |
| 5,616,502 | A * | 4/1997 | Haugland et al. ............. 436/86 |
| 5,635,358 | A | 6/1997 | Wilding et al. |
| 5,637,469 | A | 6/1997 | Wilding et al. |
| 5,699,157 | A | 12/1997 | Parce |
| 5,716,825 | A | 2/1998 | Hancock et al. |
| 5,750,015 | A | 5/1998 | Soane et al. |
| 5,753,094 | A * | 5/1998 | Alter et al. ................. 204/451 |
| 5,759,369 | A * | 6/1998 | Menchen et al. ........... 204/456 |
| 5,779,868 | A | 7/1998 | Parce et al. |
| 5,800,690 | A | 9/1998 | Chow et al. |
| 5,842,787 | A | 12/1998 | Kopf-Sill et al. |
| 5,852,495 | A | 12/1998 | Parce |
| 5,869,004 | A | 2/1999 | Parce et al. |
| 5,876,675 | A | 3/1999 | Kennedy |
| 5,880,071 | A | 3/1999 | Parce et al. |
| 5,882,465 | A | 3/1999 | McReynolds |
| 5,885,432 | A * | 3/1999 | Hooper et al. ............. 204/469 |
| 5,885,470 | A | 3/1999 | Parce et al. |
| 5,942,443 | A | 8/1999 | Parce et al. |
| 5,948,227 | A | 9/1999 | DuBrow |
| 5,955,028 | A | 9/1999 | Chow |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,291 | A | 9/1999 | Jensen |
| 5,964,995 | A | 10/1999 | Nikiforov et al. |
| 5,965,001 | A | 10/1999 | Chow et al. |
| 5,965,410 | A | 10/1999 | Chow et al. |
| 5,972,187 | A | 10/1999 | Parce et al. |
| 5,976,336 | A | 11/1999 | Dubrow et al. |
| 5,989,402 | A | 11/1999 | Chow et al. |
| 6,001,231 | A | 12/1999 | Kopf-Sill |
| 6,004,515 | A | 12/1999 | Parce et al. |
| 6,011,252 | A | 1/2000 | Jensen |
| 6,012,902 | A | 1/2000 | Parce |
| 6,042,709 | A | 3/2000 | Parce et al. |
| 6,042,710 | A | 3/2000 | Dubrow |
| 6,046,056 | A | 4/2000 | Parce et al. |
| 6,048,498 | A | 4/2000 | Kennedy |
| 6,062,261 | A * | 5/2000 | Jacobson et al. ........... 137/827 |
| 6,103,199 | A * | 8/2000 | Bjornson ................... 422/100 |

OTHER PUBLICATIONS

Dasgupta, P.K. et al., "Electroosmosis: A Reliable Fluid Propulsion System for Flow Injection Analysis," *Anal. Chem.* 66:1792–1798 (1994).

Effenhauser, C.S. et al., "Glass Chips for High–Speed Capillary Electrophoresis Separations with Submicrometer Plate Heights," *Anal. Chem.* 65:2637–2642 (1993) Oct.

Effenhauser, C.S. et al., "High–Speed Separation of Antisense Oligonucleotides on a Micromachined Capillary Electrophoresis Device," *Anal. Chem.* 66:2949–2953 (1994) Sept.

Fan, Z.H. et al., "Micromachining of Capillary Electrophoresis Injectors and Separators on Glass Chips and Evaluation of Flow at Capillary Intersections," *Anal. Chem.* 66:177–184 (1994) Jan.

Ghandi, S.K., *VLSI Fabrication Principles*, Chapter 10, pp. 534–565, J. Wiley & Sons, (1994).

Harrison, D.J. et al., "Micromachining a Miniaturized Capillary Electrophoresis–Based Chemical Analysis System on a Chip," *Science* 261–895–897 (1993) Aug.

Harvey, M.D. et al., "Subnanomolar detection limit for sodium dodecyl sulfate–capillary gel electrophoresis using a fluorogenic, noncovaltent dye," Manuscript received Jun. 12, 1998.

Harvey, M.D. et al., "Subnanomolar detection limit for sodium dodecyl sulfate–capillary gel electrophoresis using a fluorogenic, noncovaltent dye," *Electrophoresis* 19:2169–2174 (1998).

Jacobson, S.C. et al., "Effects of Injection Schemes and Column Geometry on the Performance of Microchip Electrophoresis Devices," *Anal. Chem.* 66:1107–1113 (1994) Apr.

Jacobson, S.C. et al., "High Speed Separations on a Microchip," *Anal. Chem.* 66:1114–1118 (1994) Apr.

Jacobson, S.C. et al., "Open Channel Electrochromatography on a Microchip," *Anal. Chem.* 66:2369–2373 (1994) Jul.

Jacobson, S.C. et al., "Precolumn Reactions with Electrophoretic Analysis Integrated on a Microchip," *Anal. Chem.* 66:4127–4132 (1994) Dec.

Jacobson, S.C. et al., "Fused Quartz Substrates for Microchip Electrophoresis," *Anal. Chem.* 67:2059–2063 (1995) Jul.

Manz, A. et al., "Miniaturized Total Chemical Analysis Systems: A Novel Concept for Chemical Sensing," *Sensors and Actuators* B1:244–248 (1990).

Manz, A. et al., "Micromachining of Monocrystalline Silicon and Glass for Chemical Analysis Systems," *Trends in Anal. Chem.* 10(5):144–149 (1991).

Manz, A, et al., "Planar Chip Technology for Miniaturization and Integration of Separation Techniques into Monitoring Systems," *J. Chromatog.* 593:253–258 (1992).

Manz, A. et al., "Electroosmotic pumping and electrophoretic separations for miniaturized chemical analysis systems," *J. Micromech. Microeng.* 4:257–265 (1994).

Ramsey, J.M. et al., "Microfabricated chemical measurement systems," *Nature Med.* 1:1093–1096 (1995) Oct.

Seiler, K. et al., "Planar Glass Chips for Capillary Electrophoresis: Repetitive Sample Injection, Quantitation, and Separation Efficiency," *Anal. Chem.* 65:1481–1488 (1993) May.

Seiler, K. et al., "Electroosmotic Pumping and Valveless Control of Fluid Flow Within a Manifold of Capillaries on a Glass Chip," *Anal. Chem.* 66:3485–3491 (1994) Oct.

Woolley, A.T. et al., "Ultra High Speed Separations on a Microchip," *Proc. Nat'l. Acad. Sci. USA* 91:11348–11352 (1994) Nov.

Woolley, A.T. et al., "High Speed DNA Genotyping Using Microfabricated Capillary Array Electrophoresis Chips," *Anal. Chem.* 69:2181–2186 (1997) Jun.

* cited by examiner

| | | | | | |
|---|---|---|---|---|---|
| 1 | 46.05 | 85.42 | | | |
| 2 | 55.30 | 8.02 | | | |
| 3 | 62.60 | 16.16 | | | |
| 4 | 71.70 | 9.06 | | | |
| 5 | 78.65 | 34.91 | | | |
| 6 | 83.10 | 24.78 | | | |

| | | | | | |
|---|---|---|---|---|---|
| 1 | 41.80 | 1.17 | | | |
| 2 | 65.15 | 1.56 | | | |
| 3 | 66.75 | 5.45 | | | |
| 4 | 67.45 | 2.20 | | | |
| 5 | 69.35 | 2.73 | | | |
| 6 | 77.10 | 1.62 | | | |

METHODS, DEVICES AND SYSTEMS FOR CHARACTERIZING PROTEINS

CROSS-REFERENCE TO RELATED APPLICATIONS

This application is a continuation-in-part of U.S. patent application Ser. No. 09/243,149, filed Feb. 2, 1999 now abandoned, the full disclosure of which is hereby incorporated herein by reference in its entirety for all purposes.

BACKGROUND OF THE INVENTION

The characterization of biological compounds is an inherent necessity of any endeavor that seeks to understand life, the processes that sustain life, and the events and elements that affect those processes. Typically, the understanding of life's processes, and efforts at their control, focuses first at the basic building blocks of life, namely the macromolecular compounds and complexes that differentiate living organisms from mere lifeless primordial ooze. Of particular interest in the understanding and control of life processes are the nucleic acids and the proteins they encode.

In the case of proteins, many characterization methods have remained largely unchanged for decades. For example, current protein characterization methods typically rely, at least in part, upon sodium dodecylsulfate polyacrylamide gel electrophoresis, or SDS-PAGE, to characterize proteins by their relative molecular weights. These methods employ a slab or sheet of cross-linked polyacrylamide. Proteins to be separated and characterized are mixed with a detergent buffer (SDS) and are placed at one edge of the slab, typically in a well. An electric field is applied across the slab, drawing the highly charged detergent micelle containing the proteins through the gel. Larger proteins move through the slab gel more slowly than the smaller proteins, thereby separating out from the greater micelle. After the separation, the gel is contacted with a stain, typically "coomassie blue" or a silver complexing agent, which binds to the different proteins in the gel. In the case of coomassie blue stained gels, the slab gel must be destained to remove the excess stain. These processes result in a ladder of different proteins in the slab gel, separated by size. Silver staining methods are similarly time consuming, and generally yield qualitatively, although non-quantitatively stained gels. Improvements to these processes have produced smaller gels that are faster to run, gels that are purchased "ready-to-use," and alternate staining processes. However, he basic SDS-PAGE process has remained largely unchanged as a method of protein characterization.

A number of attempts have been made to apply advances made in other areas to protein characterization. For example, capillary electrophoresis methods, which have proven successful in the analysis of nucleic acids have been attempted in the characterization of proteins. While these methods have proven capable at separating proteins, differences in available labeling chemistries, as well as fundamental structural and chemical differences between proteins and nucleic acids have created substantial barriers to the wide spread use of CE methods in protein characterization. In particular, detection of separated proteins traveling through a capillary has typically required the covalent attachment of a labeling group to all of the proteins, using relatively complex chemistry. Further, the presence of SDS in protein separations, which ensures size based separations, creates further difficulties in both labeling and separation within capillary systems.

It would be desirable to provide methods, devices, systems and kits for characterizing proteins and polypeptides, which would have enhanced throughput, sensitivity and lower space, time and reagent requirements. The present invention meets these and a variety of other needs.

SUMMARY OF THE INVENTION

In one aspect, the present invention provides methods of performing an analytical operation on a fluid first sample material. The methods typically comprise providing a microfluidic device that has a body having at least a first channel disposed therein. The first channel comprises first and second channel segments, where the first channel segment comprises a first fluid environment compatible with the performance of a first operation. The first sample material is flowed through the first channel segment to perform the first operation. It is then flowed from the first channel segment into the second channel segment. A first diluent is flowed into the second channel segment, whereby the diluent produces a second fluid environment within the second channel segment, the second environment being more compatible than the first environment with the second operation.

In a related aspect, the invention provides devices for performing analytical operations on sample materials. The devices generally comprise a body structure having a first channel segment disposed within an interior portion of the body, the first channel segment containing a first environment. The device also includes a second channel segment disposed in the body and fluidly connected to the first channel segment. At least a first diluent source is also provided fluidly coupled to the second channel segment. The devices also typically include a flow controller operably coupled to the first diluent source for delivering the first diluent into the second channel segment to provide a second environment within the second channel segment.

In another aspect, the present invention provides a method of characterizing a polypeptide, comprising providing a first capillary channel having a separation buffer disposed within. The separation buffer comprises a polymer matrix, a buffering agent, a detergent, and a lipophilic dye. The polypeptide is introduced into one end of the capillary channel. An electric field is applied across a length of the capillary channel which transports polypeptides of different sizes through the polymer matrix at different rates. The polypeptide is then detected as it passes a point along the length of the capillary channel.

Another aspect of the present invention is a device for separating polypeptides. The device is comprised of a body structure having at least a first capillary channel containing separation buffer within. The separation buffer is comprised of a polymer matrix, a buffering agent, a detergent, and a lipophilic dye capable of binding to the polypeptide or polypeptides. A port disposed in the body structure is in fluid communication with the first capillary channel in order to introduce polypeptides into the first capillary channel.

A further aspect of the present invention is a kit for use in characterizing a polypeptide. The kit is comprised of a microfluidic device hat comprises the elements of the devices described above. The separation buffer is comprised of a polymer matrix, a buffering agent, and a lipophilic dye. Each packaging contains the body structure, the separation buffer, and the lipophilic dye.

Another aspect of the present invention is a system for characterizing a polypeptide. The system includes a body structure having at least a first capillary channel containing a separation buffer disposed therein. The separation buffer is comprised of a polymer matrix, a buffering agent, a detergent, and a lipophilic dye. An electrical power source is operably coupled to opposite ends of the first capillary channel in order to apply an electric field across a length of the capillary channel. A detector is disposed in sensory communication with the capillary channel at a first point to detect the polypeptide as it passes the first point.

DETAILED DESCRIPTION OF THE INVENTION

I. Methods, Devices and Reagents

A. Generally

Figure 1:
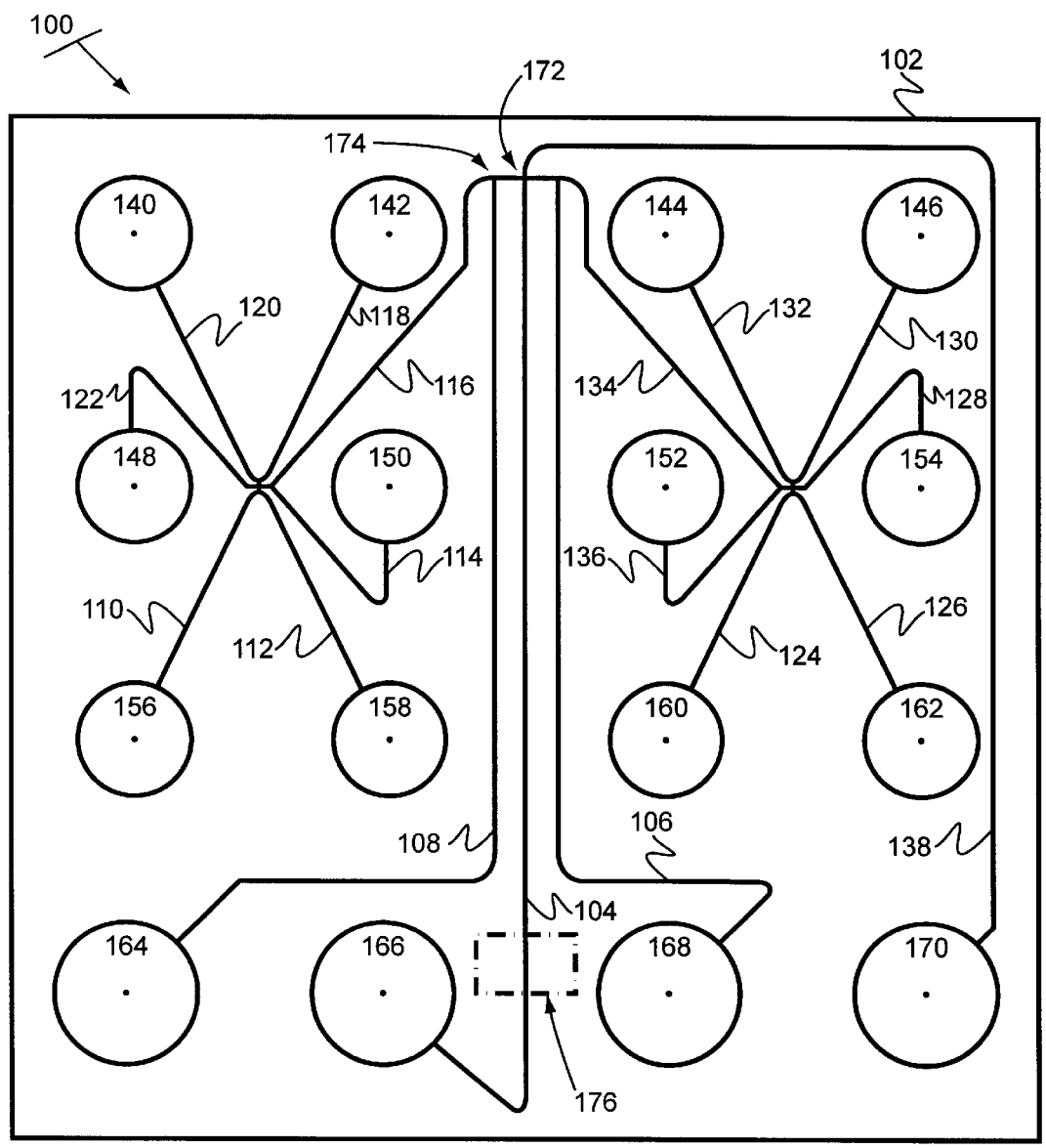
FIG. 1 illustrates a microfluidic device for use in conjunction with the present invention.

The present invention provides methods, devices, systems and kits for use in characterizing polypeptides, proteins and fragments thereof (collectively referred to herein as "polypeptides"). The methods, devices, systems and kits of the invention are particularly useful in characterizing polypeptides by their molecular weight through electrophoretic migration of the polypeptides through a polymer separation matrix that is contained within a capillary channel, also referred to in general terms as "capillary electrophoresis."

As noted previously, attempts have been made to separate proteins and polypeptides using capillary electrophoresis methods. Because capillary electrophoresis uses a closed system, e.g., a capillary, labeling of the proteins has typically been carried out prior to the separation. This has generally taken the form of covalent attachment of labeling groups to all of the proteins in the mixture to be separated. Once separated, the label upon each protein can then be detected. Covalent labeling techniques often involve complex chemistries, and at the very least, require additional steps in advance of separating the proteins. Additionally, labels are generally relatively large structures which may adversely affect the determination of a protein's molecular weight. While some have attempted to use non-covalent, associative dyes, such attempts have generally provided less than acceptable results.

In accordance with at least a first aspect of the present invention, however, methods are provided for characterizing and/or separating proteins by capillary electrophoretic methods, which are rapid, reproducible, and do not involve complex sample preparation steps prior to performing the separation. In particular, the methods of the present invention provide a first capillary channel that includes a separation buffer disposed therein, where the separation buffer includes a polymer matrix, a buffering agent, a detergent and a lipophilic dye. In accordance with preferred aspects of the invention, the detergent and buffering agent are present within the separation buffer at concentrations that are at or below the critical micelle concentration ("CMC"). By maintaining the detergent and buffer concentrations at or below the CMC, adverse effects, such as dye binding to detergent micelles can be minimized. Without being bound to a particular theory of operation, it is believed that dye binding to detergent micelles within a capillary system in previously described systems, has resulted in substantial background signal and has yielded signal irregularities during a separation, e.g., bumps and dips in a signal baseline. The methods of the present invention, on the other hand, carefully control the various components of the system to avoid or at least minimize these adverse effects. In particularly preferred aspects, the buffer and detergent are provided at a level at or below the CMC at least at the point at which the separated components of the operation are to be detected, thereby avoiding the dye binding to the micelles that gives higher background signals. This can be a result of the overall system being maintained and/or run at levels below the CMC, e.g., buffer and detergent concentrations, or it can be a result of an in situ treatment of the sample, buffer, detergent fluids, e.g., dilution, reagent addition or other solution modification, which reduces the separation buffer in the detected portion of the system to a level below the CMC.

In practice, the protein or polypeptide sample that is to be analyzed and or characterized, is typically pretreated to denature the protein and provide adequate coating of the protein by the detergent, as well as provide adequate labeling of the coated proteins in the sample.

The protein or polypeptide that is to be characterized (or mixture of polypeptides that are to be separated) are then introduced into the capillary channel, typically at one end of a channel segment. By applying an electric field across the length of the capillary channel, polypeptides of different size will migrate through the polymer solution at different rates. The polypeptides, which are coated in detergent that has a substantial charge associated with it, will migrate in one direction through the capillary channel. Polypeptides of different molecular weights, however, will migrate through the polymer solution at different rates, and will be separated out. While traveling through the separation buffer in the channel, the polypeptides will pick up the lipophilic dye that is present within the separation buffer, as well as bringing any associated dye which was optionally included with the sample, e.g., during sample pretreatment, dilution or the like.

In the context of the separation, once separated from each other, the polypeptides, which at this point have a level of an associative lipophilic dye associated with them, can be detected by virtue of that dye, at a point in the capillary channel downstream of the point at which they were introduced.

B. Sample Pretreatment

As noted above, prior to their characterization, protein or polypeptide containing samples are typically pretreated with an appropriate detergent containing buffer. In particularly preferred aspects, the polypeptide sample mixture is pretreated in a buffer that comprises the same buffering agent as the separation buffer and the same detergent that is used in the separation buffer, in order to ensure denaturation of the protein prior to its separation. Denaturation of the protein ensures a linear molecule during separation, so that the separation profile of a protein is more closely related to its molecular weight, regardless of whether the native protein is globular, linear, filamentous, or has some other conformation. Pretreatment is typically carried out in the presence of detergent at a concentration that is greater than the protein concentration of the sample (w/v), and preferably greater than about 1.4× of the protein concentration (w/v) in the sample.

In order to avoid interfering effects of detergent bound dye, it is often desirable to perform sample pretreatment in a detergent concentration that is less than or approximately equal to the concentration of detergent in the running buffer, from about 0.05× to about 3×, of the detergent concentration of the running buffer.

In preferred aspects, the concentration of SDS in the pretreatment buffer is less than that used in the running buffer. Thus, the sample pretreatment is typically carried out in the presence of a detergent concentration of between about 0.05% and 2%, preferably, between about 0.05% and about 1% and more preferably, less than about 0.5%. If the sample material is then diluted in the loaded sample, e.g., from about a 1:2 to about a 1:20 dilution, this results in a detergent level in the loaded sample of between about 0.0025 to about 1% detergent, preferably, from about 0.0025% to 0.5%, and again, more preferably less than about 0.5%.

Figure 6:
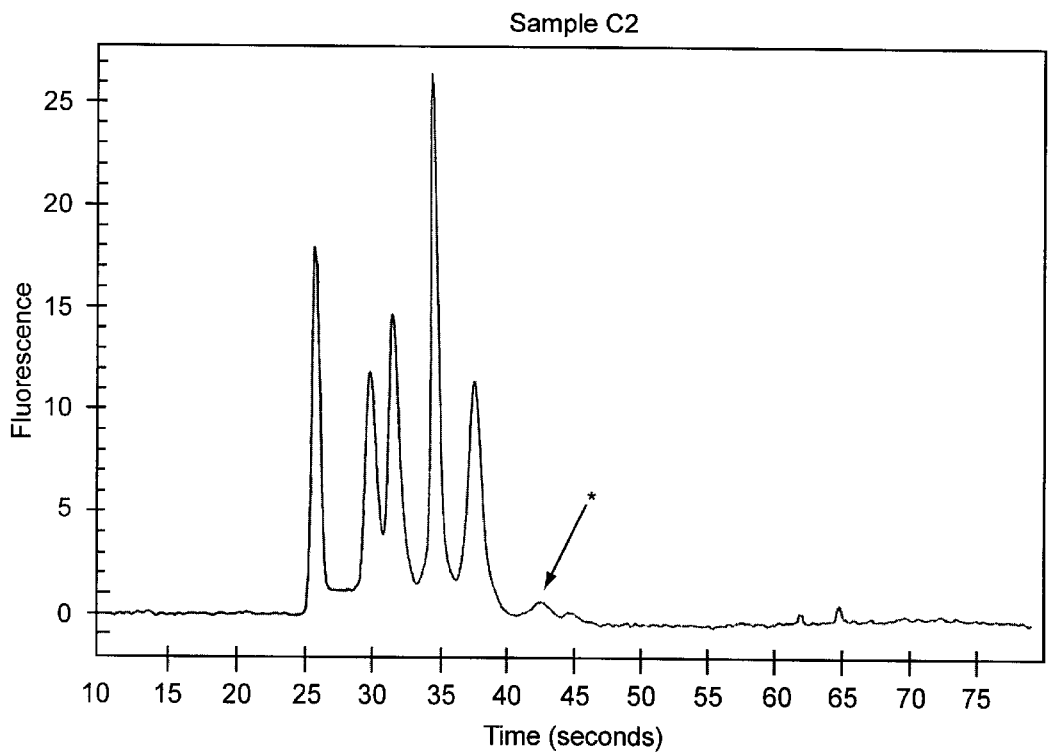
FIG. 6 is a chromatogram of molecular weight standards showing the detergent-dye front peak.

These levels are in contrast to conventional SDS-PAGE separations where samples are pretreated in detergent concentrations that can be upwards of 5 to 20 times that of the separation buffer. In particular, sample pretreatment for typical SDS-PAGE methods is generally carried out in loading buffers that have detergent, e.g., SDS, concentrations of 2% or greater (See, e.g., U.S. Pat. No. 5,616,502) in 50 mM buffer, while the running buffer contains only 0.1% detergent. Use of these relatively high detergent levels in the loading buffer as compared to the running buffer when used in capillary systems as described herein however, gives rise to a much larger interfering detergent front that tends to co-elute with polypeptides having molecular weights in a desirable range. For example, FIG. 6 shows a chromatogram of a set of molecular weight standards (see Examples section, below). In the example shown, the peak associated with the detergent front eluted at approximately 43 seconds, which would correspond to the elution time for proteins or polypeptides having molecular weights in the range of 60 to 70 kD, an important molecular weight range in protein analyses.

By reducing the concentration of detergent in the sample pretreatment step, any interfering peak is also reduced. This has proven effective despite the previously held belief in the art that sample pretreatment required high levels of detergent, e.g., 2% or higher. Further, controlling the ionic strength and detergent concentration of the sample pretreatment and separation buffers in accordance with the parameters set forth herein, allows one to somewhat control the elution profile of the detergent front, e.g., causing its elution before or after the polypeptides that are to be characterized.

Also in preferred aspects, the detergent used in pretreatment is the same detergent used in the separation buffer, e.g., SDS. Generally, pretreatment conditions can be varied depending upon the conditions of the overall separation, e.g., the nature of the proteins to be separated, the medium in which the samples are disposed, e.g., buffer and salt concentrations, and the like, as described for the separation buffers, below. In particular, SDS and salt concentrations may be varied, e.g., within the parameters set forth herein, so as to optimize for a given separation.

B. Separation Buffers

In accordance with the present invention, a separation buffer is used in carrying out the methods described herein, which buffer comprises a polymer matrix, a buffering agent, a detergent and a lipophilic dye. A variety of polymer matrices can be used in accordance with the present invention, including cross-linked and/or gellable polymers. However, in preferred aspects, non-crosslinked polymer solutions are used as the polymer matrix. Non-crosslinked polymer solutions that are suitable for use in the presently described methods have been previously described for use in separation of nucleic acids by capillary electrophoresis, see e.g., U.S. Pat. Nos. 5,264,101, 5,552,028, 5,567,292, and 5,948,227, each of which is hereby incorporated herein by reference. Such non-crosslinked or "linear" polymers provide advantages of ease of use over crosslinked or gelled polymers. In particular, such polymer solutions, because of their liquid nature, are more easily introduced into capillary channels and are ready to be used, whereas gelled polymers typically require a cross-linking reaction to occur while the polymer is within the capillary.

Generally, the most commonly utilized non-crosslinked polymer solution comprises a polyacrylamide polymer, which preferably is a polydimethylacrylamide polymer solution which may be neutral, positively charged or negatively charged. In particularly preferred aspects, a negatively charged polydimethylacrylamide polymer is used, e.g., polydimethylacrylamide-co-acrylic acid (See, e.g., U.S. Pat. No. 5,948,227). Surprisingly, the use of polydimethylacrylamide polymer solutions does not result in any smearing of the proteins/polypeptides that are being separated in a capillary system. Without being bound to a particular theory of operation, it is believed that the polymer solutions have a dual function in the systems described herein. The first function is to provide a matrix, which retards the mobility of larger species moving through it relative to smaller species. The second function of these polymer solutions is to reduce or eliminate electroosmotic flow of the materials within a capillary channel. It is believed that the polymer solutions do this by adsorbing to the capillary surface, thereby blocking the sheath flow, which characterizes electroosmotic flow.

Typically, the non-crosslinked polymer is present within the separation buffer at a concentration of between about 0.01% and about 30% (w/v). Of course different polymer concentrations may be used depending upon the type of separation that is to be performed, e.g., the nature and/or size of the polypeptides to be characterized, the size of the capillary channel in which the separation is being carried out, and the like. In preferred aspects, for separation of most polypeptides, the polymer is present in the separation buffer at a concentration of from about 0.01% to about 20% and more preferably, between about 0.01% and about 10%.

The average molecular weight of the polymer within the polymer solutions may vary somewhat depending upon the application for which the polymer solution is desired. For example, applications that require higher resolution may utilize higher molecular weight polymer solutions, while less stringent applications can utilize lower molecular weight polymer solutions. Typically, the polymer solutions used in accordance with the present invention have an average molecular weight in the range of from about 1 kD to about 6,000 kD, preferably between about 1 kD and about 1000 kD, and more preferably, between about 100 kD and about 1000 kD.

In addition to the percent charge and molecular weights described above, the polymers used in accordance with the present invention are also characterized by their viscosity. In particular, the polymer components of the system described herein typically have a solution viscosity as used within the capillary channel, in the range of from about 2 to about 1000 centipoise, preferably, from about 2 to about 200 centipoise and more preferably, from about 5 to about 100 centipoise.

In addition to incorporation of a non-crosslinked polymer solution, the separation buffers used in practicing the present invention also comprise a buffering agent, a detergent, and a lipophilic dye.

As noted previously, polypeptides typically vary a great deal in their physicochemical properties, and particularly in their charge to mass ratios, depending upon their amino acid composition. As such, different polypeptides will generally have different electrophoretic mobilities under an applied electric field. As such, electrophoretic separation of proteins and other polypeptides typically utilizes a detergent within the running buffer, in order to ensure that all of the proteins/polypeptides migrate in the same direction under the electric field. For example, in typical protein separations, e.g., SDS-PAGE, a detergent (sodium dodecylsulfate or SDS) is included in the sample buffer. The proteins/polypeptides in the sample are coated by the detergent which to provide the various proteins/polypeptides with a substantial negative charge. The negatively charged proteins/polypeptides then migrate toward the cathode under an electric current. In the presence of a sieving matrix, however, larger proteins will move more slowly than smaller proteins, thereby allowing for their separation.

In accordance with certain aspects of the invention, each of the detergent, buffering agent and dye components of the separation buffer is selected and provided at a concentration so as to minimize any adverse interactions among them, which interactions can interfere with the separation and characterization of proteins or polypeptides, e.g., reduce separation efficiency, signal sensitivity, production of aberrant signals, or the like. In particular, the buffering agent and detergent are typically provided at concentrations which optimize separation efficiencies of polypeptides, but which minimize background signal, and baseline signal irregularities. As noted previously, it has been observed that dye binding to detergent micelles produces a substantial level of background signal during capillary separations, as well as giving rise to various baseline irregularities, e.g., bumps and dips.

Accordingly, in a first aspect, polypeptide separation and/or characterization is accomplished by providing the buffering agent and the detergent at concentrations which are below the point at which the detergent begins to form excessive independent micelles, to which dye may bind, within the buffer solution. Typically, the concentration at which micelles begin to form is termed the critical micelle concentration ("CMC"). Restated, the CMC is the highest monomeric detergent concentration obtainable and thus, the highest detergent potential obtainable. Helenius et al., Methods in Enzymol. 56(63):734–749 (1979).

The CMC of a detergent solution decreases with increasing size of the apolar moiety (or hydrocarbon tail), and to a lesser extent, with the decreasing size and polarity of the polar groups. Helenius et al., supra. Thus, whether a detergent solution is above or below its CMC is determined not only by the concentration of the detergent, but also by the concentration of other components of the solution which can have an effect on the CMC, namely the buffering agent and ionic strength of the overall solution. Accordingly, in the methods, systems and devices of the present invention, the separation buffer is provided with a detergent concentration and a concentration of buffering agent, such that the separation buffer is maintained at or below the CMC.

Figure 3:
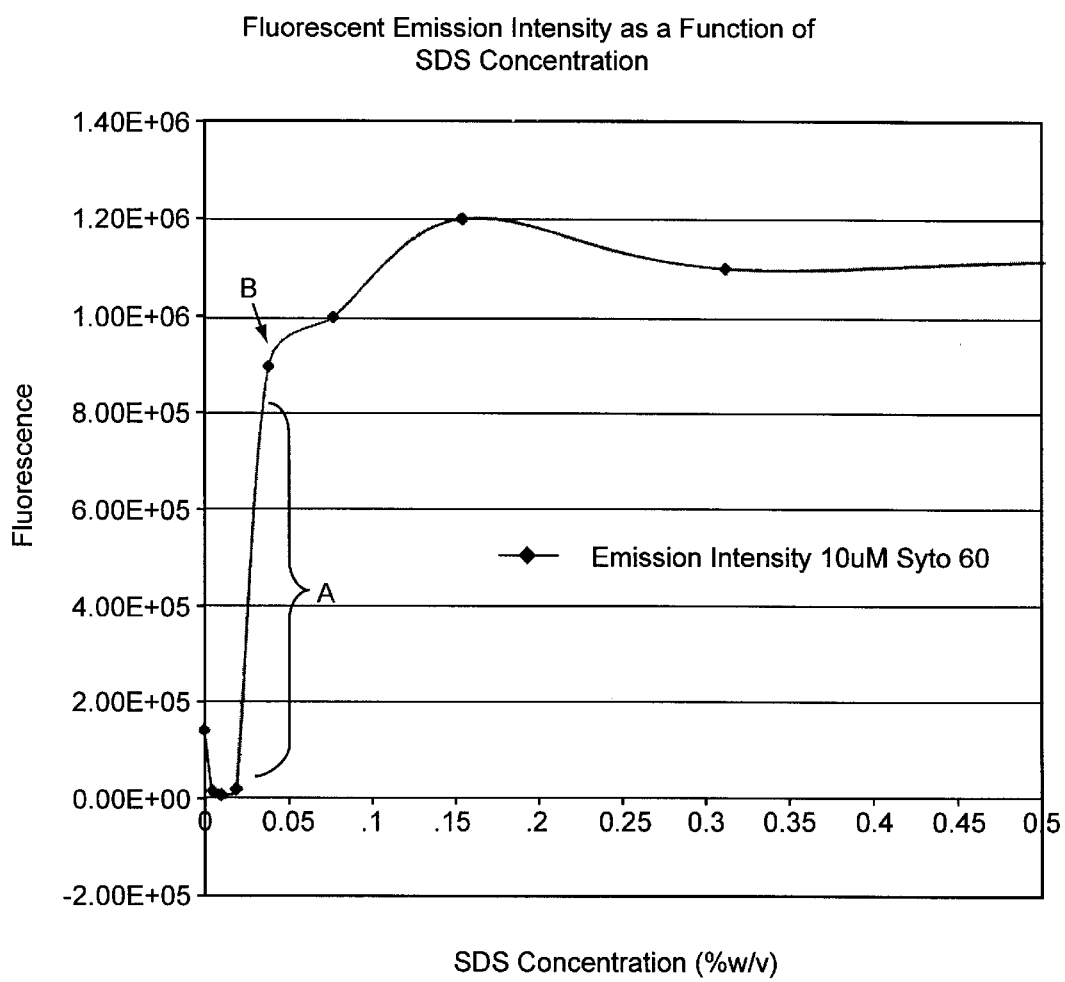
FIG. 3 illustrates a plot of fluorescence intensity versus detergent concentration for determining the critical micellar concentration of the detergent in the given buffer.

A number of methods can be used to determine whether a buffer is below its CMC. For example, Rui et al., Anal. Biochem. 152:250–255 (1986) describes the use of a fluorescent N-phenyl-1-naphthylamine dye to determine the CMC of detergent solutions. In the context of the separation buffers described herein, the detergent is typically provided at a concentration that is at or below the CMC for the separation buffer. In particularly preferred aspects, the detergent concentration is at or just below the CMC for the buffer. Determination of optimal concentration of detergent may be determined experimentally. In particular, using the lipophilic dyes described herein, one can measure the relative micelle concentration in a detergent solution by measuring the fluorescence of the solution as a function of detergent concentration. For example, FIG. 3 illustrates a plot of fluorescent intensity of SDS solutions containing 10 $\mu$M of a fluorescent lipophilic dye (Syto 61, Molecular Probes Inc.) as a function of SDS concentration. The critical micellar concentration is indicated by the steep increase in the fluorescent intensity, indicated as point A. In accordance with the present invention, therefore, where it is indicated that the detergent concentration is at or below the CMC, it is understood that the detergent concentration will be a concentration that falls either on or below the steep portion of a plot like that shown, and particularly, below the point on the curve indicated as point B, and preferably, within or below the region marked as point A.

As noted, the CMC of a detergent varies from one detergent to another, and also varies with the ionic strength of the buffer in which the detergent is disposed. In typical separation operations and buffers, the detergent concentration in the separation buffer is provided at a concentration above about 0.01% (w/v), but lower than about 0.5%, while the buffering agent is typically provided at a concentration of from about 10 mM to about 500 mM, provided that the buffer is maintained at or below the CMC.

Detergents incorporated into the separation buffer can be selected from any of a number of detergents that have been described for use in electrophoretic separations. Typically, anionic detergents are used. Alkyl sulfate and alkyl sulfonate detergents are generally preferred, such as sodium octadecyl sulfate, sodium dodecylsulfate (SDS) and sodium decylsulfate. In particularly preferred aspects, the detergent comprises SDS. In SDS embodiments, the detergent concentration is generally maintained at concentrations described above. In preferred aspects, SDS concentrations in the separation buffers are therefore typically greater than 0.01% to ensure adequate coating of the proteins in the sample, but less than about 0.5% to prevent excessive micelle formation. In preferred aspects, the detergent concentration is between about 0.02% and about 0.15%, and preferably, between about 0.03% and 0.1%.

In buffers utilizing preferred detergent concentrations, the buffering agent is typically selected from any of a number of different buffering agents. For example, buffers that are generally used in conjunction with SDS-PAGE applications are also particularly useful in the present invention, such as tris, tris-glycine, HEPES, CAPS, MES, Tricine, combinations of these, and the like. In particularly preferred aspects, however, buffering agents are selected that have very low ionic strengths. Use of such buffers allows one to increase the concentration of detergent without exceeding the CMC. Preferred buffers of this type include zwitterionic buffers, such as amino acids like histidine and Tricine, which have a relatively high buffering capacity at the relevant pH, but which have extremely low ionic strengths, due to their zwitterionic nature. Buffering agents that comprise relatively large ions having relatively low mobilities within the system are also preferred for their apparent ability to smooth out the signal baseline, e.g., using Tris as a counterion.

In the case of the preferred detergent solutions, e.g., SDS, sodium octadecylsulfate, sodium decylsulfate, and the like, at the above-described concentrations, the buffering agent is typically provided at concentrations between about 10 MM and about 200 mM, and preferably at a concentration of between about 10 mM and about 100 mM. In particularly preferred aspects, Tris-Tricine is used as the buffering agent at a concentration of between about 20 mM and about 100 mM.

With reference to the foregoing discussion, it can be seen that the most preferred separation buffer comprises SDS at a concentration of between about 0.03% and about 0.1%, and Tris-Tricine as the buffering agent, at a concentration of between about 20 mM and about 100 mM, with each being provided such that the buffer is at or below the CMC, when operating under the normal operating conditions of the overall system/method.

In addition to the foregoing components, the separation buffer also typically comprises an associative dye or other detectable labeling group, which associates with the proteins and polypeptides that are to be characterized/separated. This enables the detection of proteins and/or polypeptides as they are traveling through the separation buffer. As used herein, an "associative dye" refers to a detectable labeling compound or moiety, which associates with a class of molecules of interest, e.g., a protein or peptide, preferentially with respect to other molecules in a given mixture. In the case of protein or polypeptide characterization, lipophilic dyes are particularly useful as protein or polypeptide associative dyes.

Examples of particularly preferred lipophilic dyes for use in the present invention include fluorescent dyes, e.g., merocyanine dyes, such as those described in U.S. Pat. No. 5,616,502, which is incorporated herein by reference. Particularly preferred dyes include those that are generally commercially available from Molecular Probes, Inc. (Eugene Oreg.) as the Sypro Red™, Sypro Orange™, and Syto 61™ dyes. Such dyes are generally intended for use in staining slab gels, in which one can wash away excess dye, and eliminate any adverse effects of SDS in the gel, e.g., through washing. However, surprisingly, it has been discovered by the present inventors, that these dyes are particularly useful in SDS capillary gel electrophoresis (SDS-CGE), giving surprising sensitivity and with little or no "smearing" or interference from the detergent, when the buffers are formulated as described herein.

Further, and more unexpected than the compatibility of the dyes with the separation buffer, is that the incorporation of the lipophilic dye into the separation buffer within the capillary channel does not create excessive background signal which would reduce the sensitivity of the assay. In particular, by providing the dye within the separation buffer one would expect to observe a relatively high background signal from the dye that is in the buffer. Accordingly, one would expect to be required to include the dye within the sample solution, but not within the separation buffer in the channel. However, this latter techniques results in an extremely low signal level during separation. By including the dye in the separation buffer within the capillary channel, signal is maintained high while background is maintained surprisingly low. The lipophilic dyes used in the present invention are generally present within the separation buffer at concentrations between about 0.1 $\mu$M and 1 mM, more preferably, between about 1 $\mu$M and about 20 $\mu$M.

C. Post-Separation Treatment

In contrast to the methods described above, wherein the sample is pretreated and separated under buffer and detergent concentrations that are optimized for the dye system utilized, e.g., maintained below the CMC of the particular detergent, in certain aspects, the buffer/detergent conditions in which the sample components exist are altered after separation of those components and during or immediately prior to detection of those components, whereupon the adverse effects of detergent micelles are reduced or eliminated. Specifically, sample components, e.g., polypeptides are separated under optimized separation buffer and detergent conditions or concentrations that may be at, above or below the CMC. Once the sample components are separated, these conditions are altered such that the buffer and/or detergent concentrations at the detection point are optimized for the detection step, for example reducing those levels to a level below the CMC. In particular, often, once the detergent level and/or buffer concentrations are adjusted below the CMC, the micelles disperse and the adverse effects of dye binding to micelles are reduced or eliminated.

Typically, in the case of polypeptide separations, altering the environment is carried out by adding one or more diluents into the separated sample components prior to their passing the detector, such that the sample-containing separation buffer is at or below the CMC. This is optionally done by altering the ratio of detergent and buffering agent to elevate the CMC to at or above the operating concentration of detergent, and/or dilute the detergent level such that it falls below the CMC. Thus, the diluent may add to, maintain or reduce the concentration of buffering agent while typically reducing the level of detergent, or it may maintain the detergent concentration while reducing the concentration of buffering agent. In either instance, the desired goal is to eliminate detergent micelles at the point and time of detection. In a similar fashion, materials may be added that effectively break up detergent micelles, e.g., co-detergents.

Where post-separation treatment is used, the separation buffer composition can span a wider range of buffer and detergent concentrations. For example, the separation buffer typically includes a buffering agent, e.g., as described above, at concentrations from about 10 to about 200 mM, and detergent concentrations of from about 0.01 to about 1.0%, and typically above the CMC, e.g., above about 0.05% and preferably above about 0.1%. Detection of lipophilic dyes, on the other hand, is preferably carried out in the absence of excessive detergent micelles, which bind the dye and contribute to excessive background signals. Thus, dilution of the separation buffer is typically practiced to reduce the detergent concentration to a level below the CMC of the detergent, e.g., less than about 0.1%. Accordingly, the dilution step preferably dilutes the separation buffer from about 1:2 to about 1:30 prior to detection. While this also dilutes the sample components to be detected, the substantial reduction in background as a result of the dilution enables easy detection at very low levels of sample material.

Figure 7:
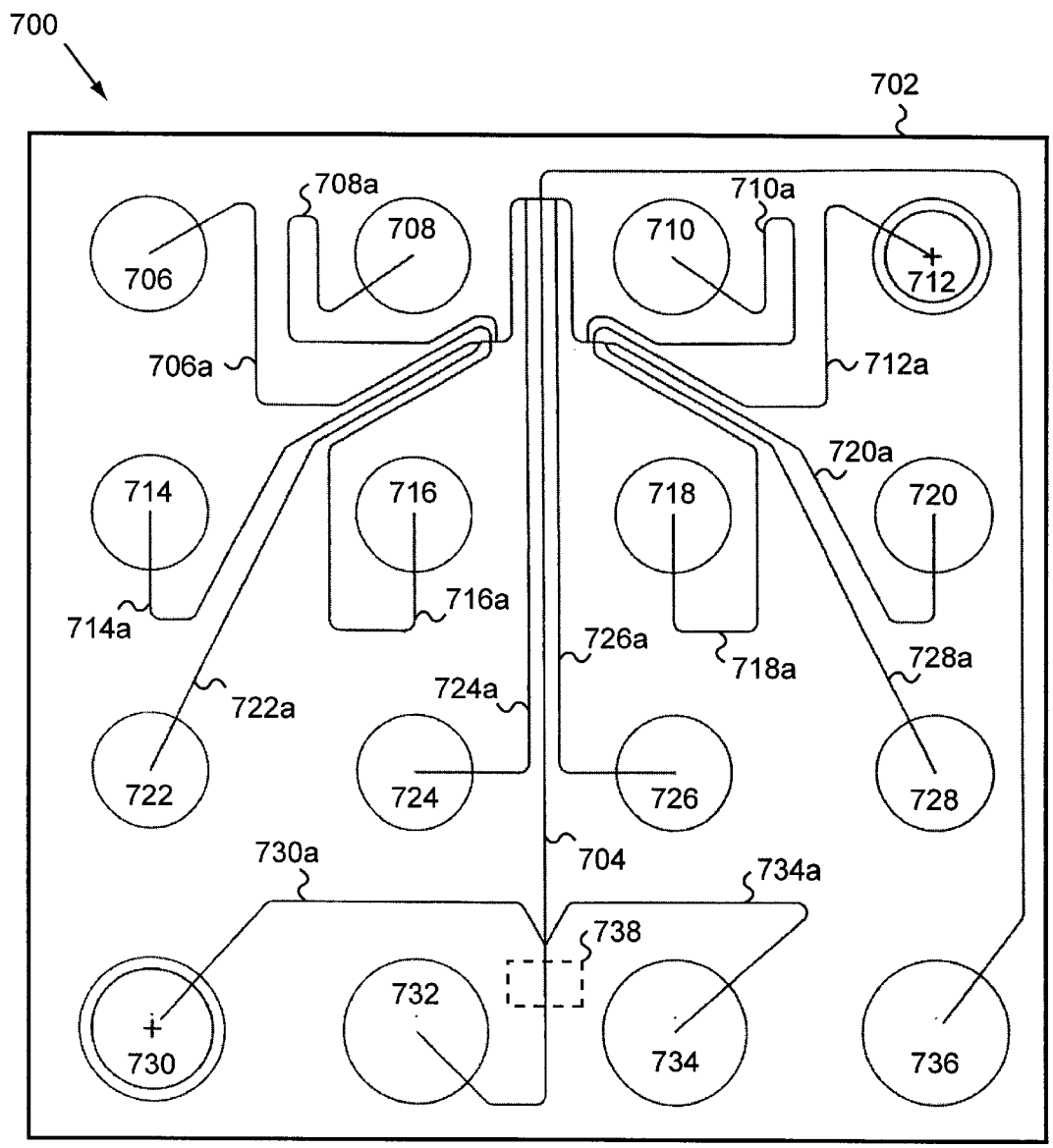
FIG. 7 is a schematic illustration of a microfluidic device for performing a post separation treatment in accordance with the methods described herein.

In accordance with this aspect of the invention, microfluidic devices are particularly well suited for carrying out these methods. In particular, the inclusion of integrated fluid channel networks permits the ready addition of diluents and other reagents into flowing streams of materials. Specifically, diluent channels are provided immediately upstream of the detection zone so as to deliver diluent into the detection zone along with the separated sample components. The sample components are then detected in the absence of interfering detergent micelles. An example of a particularly preferred channel layout for a microfluidic device for accomplishing this post separation treatment is shown in FIG. 7, and described in greater detail, below. As used herein, the terms "upstream" and "downstream" refer to the relative positioning of the element so described when considered in the context of the direction of flow of the material of interest, e.g., fluid, sample components, etc., during normal operation of the system being described. Typically, the phrase upstream refers to the direction toward the sample or buffer reservoir connected to a particular channel, while downstream refers to the direction of the waste reservoir connected to a particular channel.

D. Capillary Channels and Devices

1. Generally

The present invention also provides devices and systems for use in carrying out the above described protein characterization methods. The devices of the present invention typically include a supporting substrate which includes a separation zone into which is placed the separation buffer. A sample that is to be separated/characterized is placed at one end of the separation zone and an electric field is applied across the separation zone, causing the electrophoretic separation of the proteins/polypeptides. within the sample. The separated proteins/polypeptides are then separately detected by a detection system disposed adjacent to and in sensory communication with the separation zone.

2. Conventional Capillary Systems

In at least a first aspect, the methods of the present invention are applicable to conventional capillary-based separation systems. Accordingly, in these aspects, the supporting substrate typically comprises a capillary tube, e.g., fused silica, glass or polymeric capillary tube, which includes a capillary channel disposed through it. At least a portion of the capillary channel in the tube comprises the separation zone of the capillary. Separation buffer is placed into the capillary channel by, e.g., pressure pumping, capillary action or the like, and the sample to be separated/characterized is injected into one end of the capillary channel. One end of the capillary tube is then placed into fluid contact with a cathode reservoir (having a cathode in contact with the reservoir) at one end and with an anode reservoir (having an anode in contact with the reservoir) at the other, and an electric field is applied through the capillary tube to electrophorese the sample material through the capillary tube and the contained separation buffer. As the proteins and polypeptides travel through the separation buffer they associate with the lipophilic dye which is then detected toward the cathode end of the capillary channel by the detection system.

In the case of a post separation treatment step, e.g., as described above, additional buffer solutions are typically introduced into the flow path of the sample components post separation, by connecting additional flow paths or capillaries to the main separation capillary, such that the separated components exiting the separation capillary are mixed with the additional buffers or diluents. A detection chamber or capillary is also connected at this junction, such that all of the materials flow into the detection zone to be detected.

3. Microfluidic Devices

In particularly preferred aspects, the methods of the invention are carried out in a microfluidic device that provides a network of microscale capillary channels disposed within a single integrated solid substrate. In particular, the supporting substrate typically comprises an integrated body structure that includes a network of one or more microscale channels disposed therein, at least one of which is a separation channel. The separation buffer is placed within at least the separation channel. In preferred aspects, the microfluidic channel network comprises at least a first separation channel that is intersected by at least a first sample injection channel. The intersection of these two channels forms what is termed an "injection cross." In operation, the sample material is injected through the injection channel and across the separation channel. The portion of the material within the intersection is then injected into the separation channel whereupon it is separated through the separation buffer. A detector is disposed adjacent the separation channel to detect the separated proteins.

In particularly preferred aspects, the microfluidic devices used in accordance with the present invention comprise a plurality of sample wells in fluid communication with a sample injection channel which, in turn, is in fluid communication with the separation channel. This allows he analysis of multiple different samples within a single integrated microfluidic device. Examples of particularly preferred microfluidic devices for use in accordance with the present invention are shown and described in commonly owned U.S. patent application Ser. No. 09/165,704, filed Oct. 2, 1998, which is incorporated herein by reference in its entirety for all purposes. An example of such a microfluidic device is illustrated in FIG. 1. As shown, the device 100, comprises a planar body structure 102 which includes a plurality of interconnected channels disposed within its interior, e.g., channels 104–138. A number of reservoirs 140–170 are also disposed in the body structure 202 and are in fluid communication with the various channels 104–138. Samples to be analyzed and buffers are placed into these reservoirs for introduction into the channels of the device.

In operation, the separation buffer to be used in the separation/characterization is first placed into one reservoir, e.g., reservoir 166, and allowed to wick into all of the channels of the device, thereby filling these channels with the separation buffer. Samples that are to be separated/characterized are separately placed into reservoirs 140–162. The separation buffer is then placed into reservoirs 164, 168 and 170 and is already present in reservoir 166. Through the application of appropriate electric currents, the first sample material is transported or electrophoresed from its reservoir, e.g., reservoir 140, to and through the main injection intersection 172 for channel 104, via channel 120 and 116. This is generally accomplished by applying the current between reservoir 140 and 168. Low level pinching currents are typically applied at the intersection in order to prevent diffusion of the sample material at the intersection, e.g., by supplying a low level of current from reservoirs 166 and 170 toward reservoir 168 (see, e.g., WO 96/04547). After a short period of time, the current is switched such that the material in the intersection is electrophoresed down the main analysis channel 104, e.g., by applying the current between reservoirs 170 and 166. Typically, a slight current is applied after the injection to pull material in channels 116 and 134 back from the intersection, to avoid leakage into the separation channel. While the first sample is being electrophoresed down the main channel 104, the next sample to be analyzed is preloaded by electrophoresing the sample material from its reservoir, e.g., reservoir 142, toward preload reservoir 164 through the preload intersection 174. This allows for only a very short transit time to move the sample material from its preloaded position to the injection intersection 172. Once the first sample analysis is completed, the second sample material is electrophoresed across the injection intersection 172 and injected down the main analysis channel, as before. This process is repeated for each of the samples loaded into the device.

A detection zone 176 is typically provided along the main analysis channel 104, in order to provide a point at which signal may be detected from the channel. Typically, the devices described herein are fabricated from transparent materials. As such, the detection window for optically detected analyses can be located at virtually any point along the length of the analysis channel 104. As the separated sample passes the detection window, the lipophilic dye that is associated with the polypeptide fragments is detected. The amount of time required for each polypeptide fragment to travel through the separation channel then allows for the characterization of the particular polypeptide, e.g., as a measure of its molecular weight. In particular, the retention time of an unknown polypeptide is compared to the retention time of known molecular weight standards, and the approximate molecular weight of the unknown can be thereby determined, e.g., interpolated or extrapolated from the standards.

As noted previously, the post-separation treatment methods described herein are particularly advantaged by the use of microfluidic channel systems. Specifically, coupling of sources of diluent to the main separation channel is a simple matter of providing channels connected to that channel at the appropriate location, e.g., at a point that falls after the separation has occurred, but before the detection zone or window. An example of a microfluidic channel network for accomplishing this is illustrated in FIG. 7. As shown, the microfluidic device 700 includes a body 702 that includes a channel network disposed within its interior portion. Typically, the device shown in FIG. 7 will be fabricated in the same manner described above with reference to FIG. 1. The channel network includes a main channel 704 that is in fluid communication a plurality of different sample material reservoirs 706–722 and 728 via sample channels 706a–722a and 728a, respectively. Preload/waste reservoir channel/reservoirs 724/724a and 726/726a are also shown. The main channel 704 is connected to a buffer reservoir 736 and a waste reservoir 732 and includes a detection zone 738. As shown, two diluent channels 730a and 734a are provided in communication with main channel 704, on opposite sides of the main channel 704, at a point immediately upstream (in the direction of operational flow of material) from the detection zone, but downstream of the major portion of the main channel 704, where the function of that channel, e.g., separation, occurs. Diluent channels 730a and 734a are also in communication with diluent sources, e.g., reservoirs 730 and 734, respectively, so as to be able to deliver diluent from these sources to the main channel 704.

In operation in a polypeptide separation, where one wishes to characterize a sample, e.g., containing a polypeptide mixture, one fills the channels of the device 700 with the separation buffer. In the case of post separation treatment, this buffer need not adhere to the strictures defined above, because the concern over excessive micelle formation is largely lacking. Typically, in these cases, the concentration of detergent is not as important as in the pretreatment methods. In particular, the separation buffer can have higher concentrations of detergent, e.g., from about 0.1% to about 2.0%. Typically, the detergent concentration will be in excess of 0.1%. Filling the channel networks is typically carried out by depositing the separation buffer into one well, e.g., waste reservoir 732. The separation buffer then wicks throughout the channel network until it reaches each of the other reservoirs 706–730 and 734–736. Optionally, slight pressure is applied to the waste reservoir 732 to expedite filling of the channel network. An additional quantity of buffer, e.g., separation buffer, is placed into buffer reservoir 736 and load/waste reservoirs 724 and 726. A diluent material is placed into diluent reservoirs 730 and 734.

The sample material is placed into one or more of the sample reservoirs 706–722, and 728. Optionally, a number of different sample materials are placed into different reservoirs. The device is then placed into a controller/detector apparatus, e.g., a 2100 Bioanalyzer from Agilent Technologies, which directs movement of the sample materials through the channels of the device, e.g., by controlled electrokinetic methods, as described in U.S. Pat. No. 5,976,336, which is incorporated herein by reference in its entirety for all purposes. A sample placed into, e.g., reservoir 706 is moved along sample channel 706a until it crosses channel 704, and flowed toward load waste reservoir 726 via channel 726a. The portion of the sample material at the intersection of the sample loading channel 706a and the main channel 704 is then injected into the separation channel 704, and moved therethrough. Under an applied electric field, this portion of the sample that is moving through the separation buffer separates into its constituent elements as it moves along the channel 704. As it travels, the sample components, and in some cases the detergent micelles, pick up the lipophilic dye that is present in the separation buffer. Diluent buffering agents containing a lower concentration or no detergent is introduced in a continuous fashion into channel 704 via channels 730a and 734a. This diluent dilutes the separation buffer to a point that is below the CMC for the detergent, resulting in an elimination of excess detergent micelles. The diluted sample constituents bearing the lipophilic dye are then detected at the detection window 738. In some cases, fluidic dilution is accomplished through the actual introduction of fluid through the side channels. However, in preferred aspects, side channels 730a and 734a typically contain the same separation matrix present throughout the channel network. As such, dilution is carried out by the electrophoretic introduction of the ionic species from the buffering solution are introduced electrophoretically into the separation channel, to effectively dilute the species in the separation channel. In alternative aspects, the side channels 730a and 734a are provided free of any matrices, e.g., they can support pressure based or electroosmotic flow, and bulk fluid is introduced into the main channel 704, to dilute the separated sample components. As noted, the rate at which diluent is added to the channel is selected to reduce the detergent concentration in the channel at the detection point to a level below about the CMC for the detergent under the particular conditions. Typically, this comprises from about a 1:2 to about a 1:30 dilution of the detergent. Thus, in the case where the separation buffer includes, e.g., 2% SDS in a 30 mM Tris Tricine buffer, it is generally desirable to dilute the detergent level to below about 0.1% and preferably to about 0.05% SDS. Thus, the dilution is from about 2 to 3 fold to about 4 fold. Of course, as noted previously, the CMC of a particular detergent can vary depending upon the nature and concentration of the buffer.

Although described primarily in terms of diluting a polypeptide separation buffer to a point that is below the CMC of the detergent in that buffer, it will be appreciated that the post-separation treatment methods described herein are more broadly applicable. Specifically, such methods can be used in a variety of analytical operations where a subsequent operation in a chain of analytical method steps requires a different environment from the immediately preceding step or operation, which environment can be sufficiently altered by the addition of reagents, buffers, or diluents, for that subsequent operation. The above-described methods illustrate an example where the environment that is optimized for separation of polypeptides may not be optimally compatible with the optimized detection environment. Thus, in accordance with the broadest understanding of this aspect of the invention, the term "diluent refers to an added element, e.g., fluid, buffering agent, etc., that alters the environment into which it is introduced. Alteration of an environment in this sense includes changing physical properties of the environment, e.g., the presence of detergent micelles, reducing the viscosity of a solution, but also includes changing the chemical environment, e.g., titrating a buffer to yield a change in he pH of a solution, e.g., to yield a operable environment for a pH sensitive dye or other labeling species, varying a salt concentration of a solution to affect a change in hydrophobicity/hydrophilicity or to affect ionic interactions within the solution.

Similarly, labeling species may be added following an initial operation, where such labeling species might affect the previous operation. One example of such labeling includes, for example, addition of labeled antibodies to specific proteins, thereby allowing the system to function as a chip-based western blotting system. Specifically, following protein separation, a labeled antibody is added to the separated proteins just prior to detection, to preferentially associate with a protein bearing a recognized epitope. The protein is then detected by virtue of its size, and its ability to be recognized by a selected antibody.

D. Overall Systems

The devices and reagents of the present invention are typically used in conjunction with an overall analytical system that controls and monitors the operation and analyses that are being carried out within the microfluidic devices and utilizing the reagents described herein. In particular, the overall systems typically include, in addition to a microfluidic device or capillary system, an electrical controller operably coupled to the microfluidic device or capillary element, and a detector disposed within sensory communication of the separation zone or channel of the device.

Figure 2:
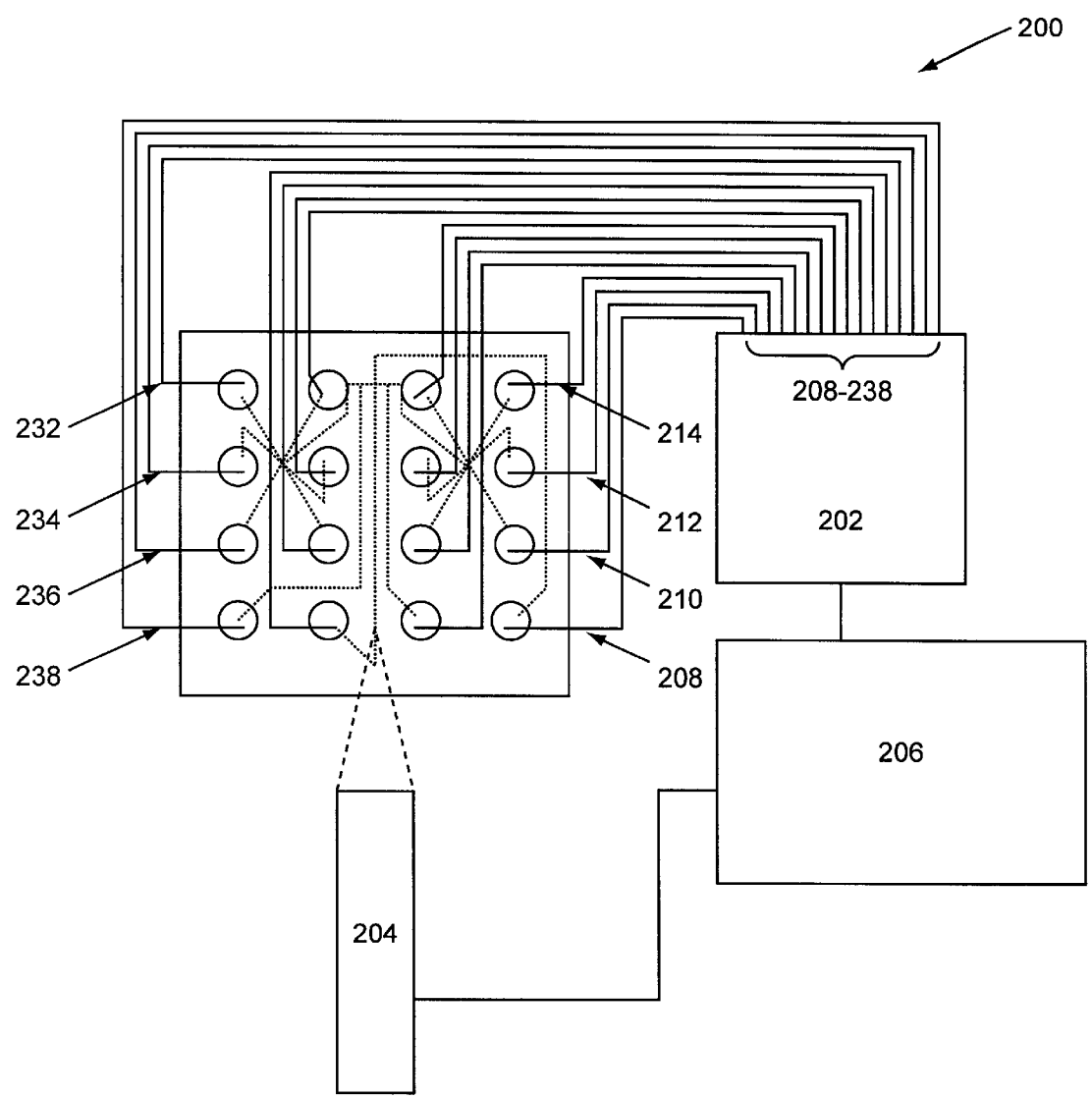
FIG. 2 illustrates an overall system for use in characterizing polypeptides according to the present invention.

An example of a system according to the present invention is shown in FIG. 2. As shown, the system 200 includes microfluidic device 100, which comprises a channel network disposed within its interior portion, where the channel network connects a plurality of reservoirs or sample/reagent wells. An electrical controller 202 is operably coupled to the microfluidic device 100 via a plurality of electrodes 204–234 which are placed into contact with the fluids in reservoirs of the microfluidic device 100. The electrical controller 202 applies an appropriate electric field across the length of the separation channel of the device to drive the electrophoresis of the sample materials, and consequent separation of the proteins and polypeptides of the invention. In the case of microfluidic devices that include intersecting channel networks, e.g., as shown, the electrical controller also applies electrical currents for moving the different materials through the various channels and for injecting those materials into other channels. Electrical controllers that provide selectable current levels through the channels of the device to control material movement are particularly preferred for use in the present invention. Examples of such "current controllers" are described in detail in U.S. Pat. No. 5,800,690, which is incorporated herein by reference.

The overall system 200 also includes a detector 204 that is disposed in sensory communication with the separation channel portion of the channel network in the microfluidic device 100. As used herein, the phrase "in sensory communication" refers to a detector that is positioned to receive a particular signal from a channel within a microfluidic device. For example, in the case of microfluidic devices that are used to perform operations that produce optical signals, e.g., chromophoric, fluorescent or chemiluminescent signals, the detector is positioned adjacent to a translucent portion of the device such that optical elements within the detector receive these optical signals from the appropriate portion of the microfluidic device. Electrochemical detectors, on the other hand, in order to be in sensory communication, typically include electrochemical sensors, e.g., electrodes, disposed within the appropriate channel(s) of the device, so as to be able to sense electrochemical signals that are produced r otherwise exist within that channel. Similarly, detectors for sensing temperature will be in thermal communication with the channels of the device, so as to sense temperature or relative changes therein. In preferred aspects, optical detectors are employed in the systems of the present invention, and more preferably, optical detectors that are configured for the detection of fluorescent signals. As such, these detectors typically include a light source and an optical train for directing an activation light at the separation channel, as well as an optical train and light sensor, for collecting, transmitting and quantifying an amount of fluorescence emitted from the separation channel. In general, a single optical train is utilized for transmission of both the activation light and the fluorescent emission, relying upon differences in wavelengths of the two types of energy to distinguish them. Generally, optical sensors incorporated into the optical detectors of the present invention are selected from these that are well known in the art, such as photomultiplier tubes (PMT) photodiodes, and the like. In particularly preferred aspects, an Agilent 2100 Bioanalyzer is used as the controller/detector system (Agilent Technologies).

The systems described herein also typically include a processor or computer 206 operably coupled to the electrical controller, for instructing the operation of the electrical controller in accordance with user instructions or preprogrammed operating parameters. The computer is also typically operably coupled to the detector for receiving and analyzing data that the detector receives from the microfluidic device. Accordingly, the computer typically includes appropriate programming for directing the operation of the electrical controller to apply electric fields to inject each of a potential plurality of samples into the separation channel. Typically, the computer also is operably coupled to the detector so as to receive the data from the detector and to record the signals received by the detector. Processor or computer 206 may be any of a variety of different types of processors. Typically, the computer/processor is a IBM PC or PC compatible computer, incorporating an microprocessor from, e.g., Intel or Advanced Microdevices, e.g., Pentium™ or K6™, or a MacIntosh™,Imac™ or compatible computer.

In the case of the polypeptide characterization methods of the present invention, the computer or processor is typically programmed to receive signal data from the detector, and to identify the signal peaks that correspond to a separated protein passing the detector. Typically, one or more internal standard proteins may be run along with the sample material. In such cases, the computer is typically programmed to identify the standard(s) e.g., by its location in the overall separation, either first or last, and to determine the molecular weights of the unknown polypeptides in the sample by extrapolation or interpolation from the standard(s). A particularly useful computer software program for use in accordance with the present invention is described for use with separation methods, in Provisional Patent Application No. 60/068,980, filed Dec. 30, 1997, and incorporated herein by reference. In the case of those embodiments run on an Agilent 2100 Bioanalyzer, the computer typically includes software programming similar to that offered used to run these systems for nucleic acid analysis.

E. Kits

The present invention also provides kits for use in carrying out the described methods. Generally, such kits include a capillary or microfluidic device as described herein. The kits also typically include the various components of the separation buffer, e.g., the non-crosslinked polymer sieving matrix, detergent, buffering agent and the lipophilic dye. These components may be present in the kit as separate volumes of preformulated buffer components, which may or may not be pre-measured, or they may be provided as volumes of combined preformulated reagents up to and including a single combination of all of the reagents, whereby a user can simply place the separation buffer directly into the microfluidic device. In addition to the buffer components, kits according to the present invention also optionally include other useful reagents, such as molecular weight standards, as well as tools for use with the devices and systems, e.g., instruments which aid in introducing buffers, samples or other reagents into the channels of a microfluidic device.

In the kit form, the reagents, device and instructions detailing the use thereof are typically provided in a single packaging unit, e.g., box or pouch, and sold together. Provision of the reagents and devices as a kit provides the user with ready-to-use, less expensive systems where the reagents are provided in more convenient volumes, and have all been optimally formulated for the desired applications, e.g., separation of high molecular weight vs. low molecular weight proteins.

The present invention is further illustrated with reference to the following examples which demonstrate certain aspects of the invention without limiting the scope of that invention.

EXAMPLES

All experiments were performed in a twelve sample microfluidic device having a single separation channel and the channel geometry illustrated in FIG. 1. Control and detection were performed using a multichannel, twelve electrode electrical controller/detector having a single point laser fluorescence detector located along the single separation channel.

Example 1

Separation of Polypeptides Using SubCMC Separation Buffer

Fluorescence data received from the separation channel was recorded by a computer (PC with Intel Pentium® microprocessor). The data was displayed in both a linear plot of fluorescence vs. time as well as in an emulated gel format generated by Caliper Technologies Corp. proprietary software.

A 0.5 M solution of Tris-Tricine buffer was prepared by dissolving Tricine in deionized water at a 0.5 M concentration, and adjusting the pH to 7.5 with 1 M Tris. The resulting buffer was then filtered through a 0.22 µm syringe filter. The sieving or separation buffer was prepared at 3% polydimethylacrylamide-coacrylic acid in 12.5 mM Tris-Tricine buffer with 0.9% (w/v) sodium dodecyl sulfate (SDS), and 10 µM Syto 60 dye (Molecular Probes, Eugene Oreg.). The separation buffer was then filtered through a Costar Spin-X™ 0.22 µm cellulose acetate centrifuge filter.

Samples were pretreated in denaturation buffer prior to placement into the reservoirs of the device. The denaturation buffer was 0.75% SDS (w/v) and 1% 2-mercaptoethanol (v/v)(BME) in 250 mM Tris-Tricine buffer. The samples were mixed 1:1 with denaturation buffer (e.g., 20 µl sample and 20 µl buffer) in a 0.5 ml microfuge tube and heated to 100° C. for 10 minutes. The heated samples were then centrifuged and vortexed. Prior to loading the samples into the wells of the microfluidic device, they were diluted 1:10 with deionized water, e.g., 1 µl sample/buffer and 9 µl water). The prepared samples therefore had a detergent concentration of 0.0375% SDS.

Figure 4:
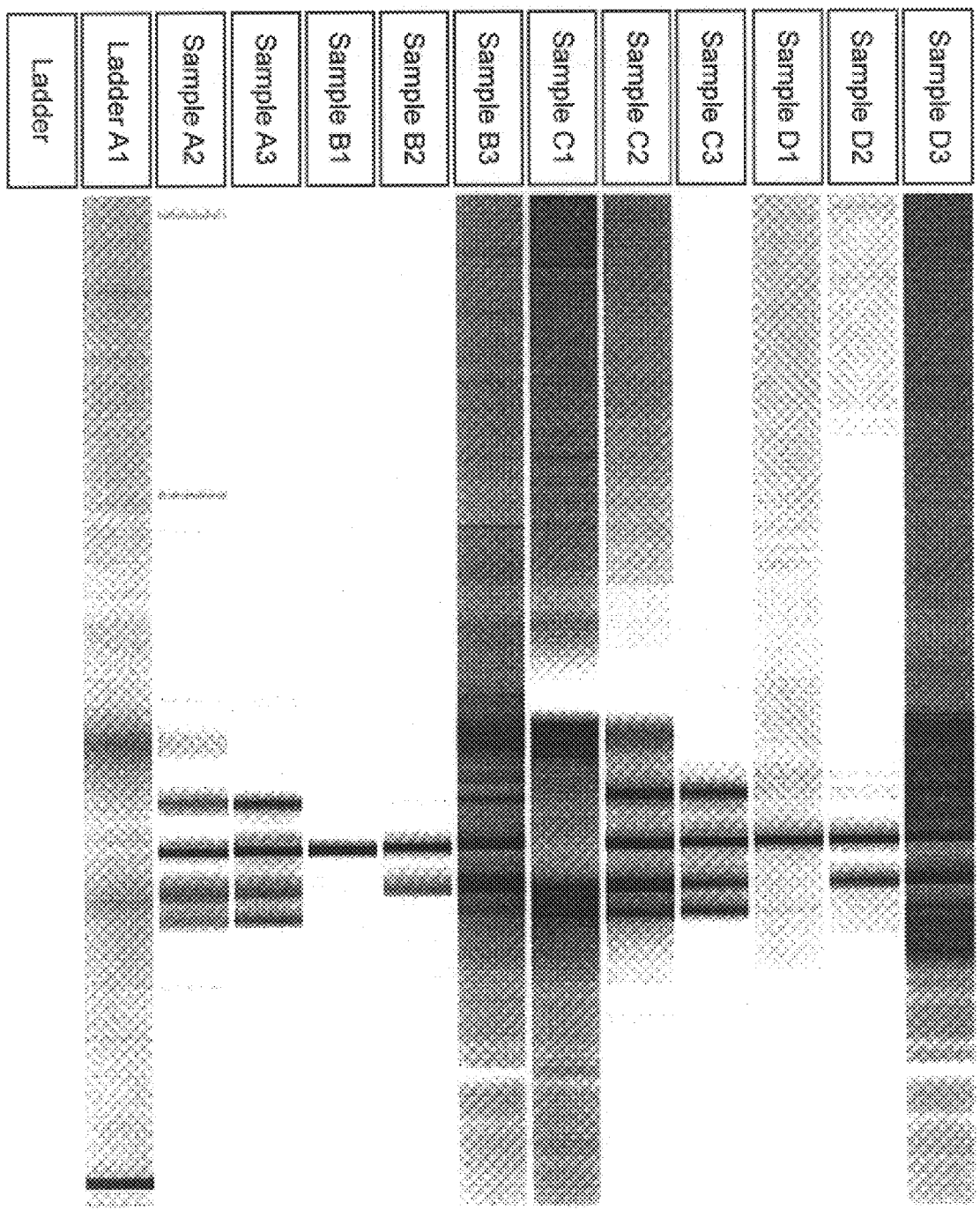
FIG. 4 illustrates a chromatogram of a protein separation performed in a microfluidic device using the methods of the invention. The chromatogram is displayed as an emulated gel, showing 12 separate separations, each as a separate lane of the emulated gel.

To prepare the microfluidic device, 7.5µl of separation buffer was pipetted into well 166 of a clean, dry device, and pressurized with a syringe to force the separation buffer into all of the channels of the device. 7.5 µl of separation buffer was then pipetted into each of wells 164, 168 and 170. 0.5 µl of the diluted samples were then separately pipetted into each of wells 140–162. In the example shown in FIG. 4, standards of known molecular weight were used. The standards included ovalbumin (45 kD), bovine carbonic anhydrase (29 kD), soybean trypsin inhibitor (21.5 kD) and α-lactalbumin (14.4 kD).

With reference to FIG. 1, wells 142 and 146 contained only buffer, and were used as blanks. A standard protein solution containing 100 µg/ml of each of the four protein standards was placed into each of wells 150 and 154, while a solution of the same four proteins at 500 µg/ml was placed into wells 158 and 162. A solution containing just the carbonic anhydrase standard at 1000 µg/ml was placed into wells 140 and 144. A solution containing both carbonic anhydrase and trypsin inhibitor at 100 µg/ml, was placed into wells 148 and 152, while a solution containing the same proteins, but at 500 µg/ml was placed into wells 156 and 160.

Each sample was separately injected down the main separation channel 104 and the separated components were detected as a function of retention time from injection. The chromatogram for each run was displayed in the form of dark bands intended to emulate a standard coomassie stained SDS-PAGE gel. Each lane of the emulated gel represents a chromatogram for a separate sample, with the dark bands indicating increases in fluorescence over background. In particular, a mixture of ovalbumin (45 kD), bovine carbonic anhydrase (29 kD), soybean trypsin inhibitor (21.5 kD) and α-lactalbumin (14.4 kD) was prepared. The two different concentrations of the four protein mix were run at 100 µg/ml (Lane A2, well 154) and 500 µg/ml (Lane A3, well 162). Separate mixtures of each of these standards were also prepared and run as follows:

Lane B1 (well 144): Carbonic Anhydrase (1 mg/ml)
Lane B2 (well 152): Trypsin Inhibitor and Carbonic anhydrase (both at 100/µg/ml)
Lane B3 (well 160): Same as B2 (both at 500 µg/ml)
Lane C2 (well 142): Same as Lane A2
Lane C3 (well 150): Same as Lane A3
Lane D1–D3 (wells 140–156): Same as B1–B3

Figure 5:
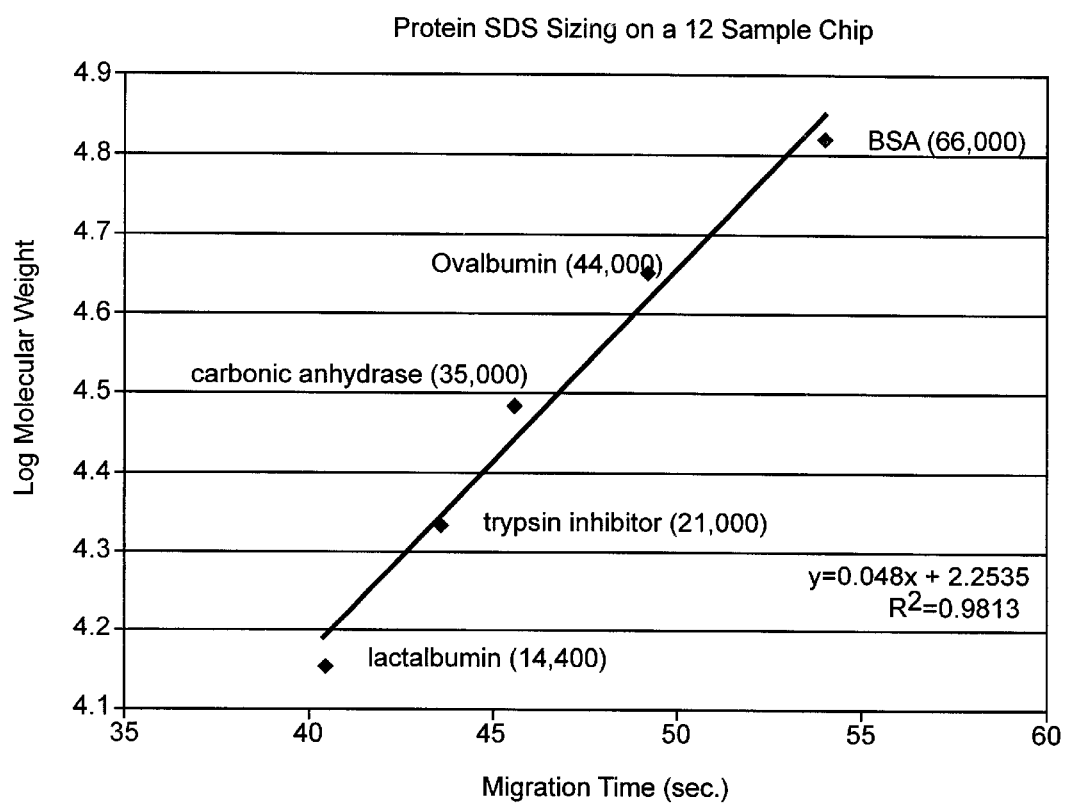
FIG. 5 is a plot of the log of the molecular weight of the standard proteins, separated as shown in FIG. 4, versus migration time.

FIG. 5 shows a plot of the log of the molecular weight versus the migration time for a set of standards run in the same fashion as described above. As can be seen, the separation methods described yield accurate, e.g., linear data, which permits the characterization of proteins of unknown molecular weight, by correlating the migration times for those unknown proteins with the set of standards, in accordance with the plot shown. As can be seen from FIGS. 4 and 5, a highly reproducible, accurate and rapid method is provided for characterizing proteins and other polypeptides.

The same set of standards, also including a Cy-5 dye marker was also run to show the co-elution of the detergent dye front. The chromatogram from this run is shown in FIG. 6. As can be seen, the detergent-dye peak (indicated with an asterisk) elutes at substantially the same time as proteins having a molecular weight of in the range of 65 kD. In those instances where the detergent concentration in the sample pretreatment buffer is at levels previously described in the art, e.g., 2%, the indicated peak is much larger, and that peak substantially interferes with the identification and quantitation of proteins in this molecular weight range.

Example 2

Separation and Detection of Polypeptides Using Post-Separation/Pre-Detection Dilution A microfluidic device as shown in FIG. 7, was filled with a separation buffer as described above. The separation channel 704 is intersected by the diluent channels 720a and 722a at point 1.2 cm downstream from the injection point, and 0.1 cm upstream of the detection point 732. The separation buffer contained 4.2% non-crosslinked polydimethylacrylamide/ co-acrylic acid in 30 mM Tris Tricine buffer, and 0.13% SDS. The dilution buffer, which comprised 30 mM Tris-Tricine with no polymer or SDS, was placed into reservoirs 720 and 722. The buffering agent was flowed into the separation channel electrokinetically, e.g., electrophoretically.

A polypeptide standard solution (10–205 kD protein standard from Bio-Rad, Inc.) was placed into a sample reservoir, e.g., reservoir 706, and loaded and injected into the separation channel using the same methods described in U.S. Pat. No. 5,976,336, previously incorporated herein.

Figure 8A:
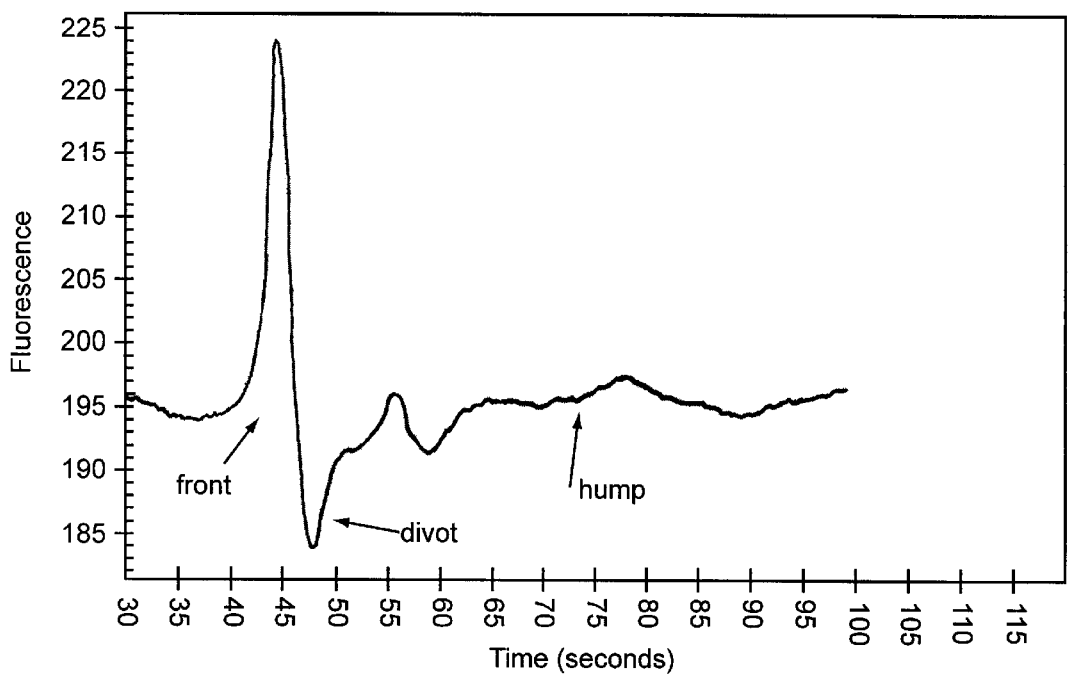
FIGS. 8 (A–D) shows plots of separation data illustrating the effects of post separation dilution.
Figure 8B:
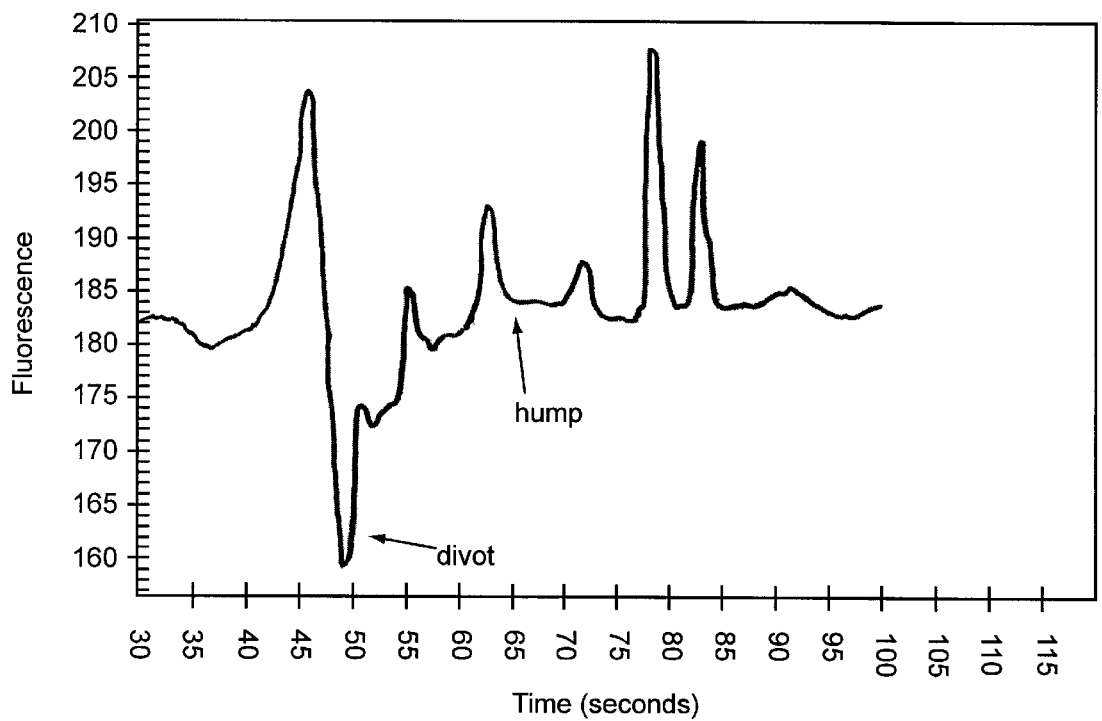
Figure 8C:
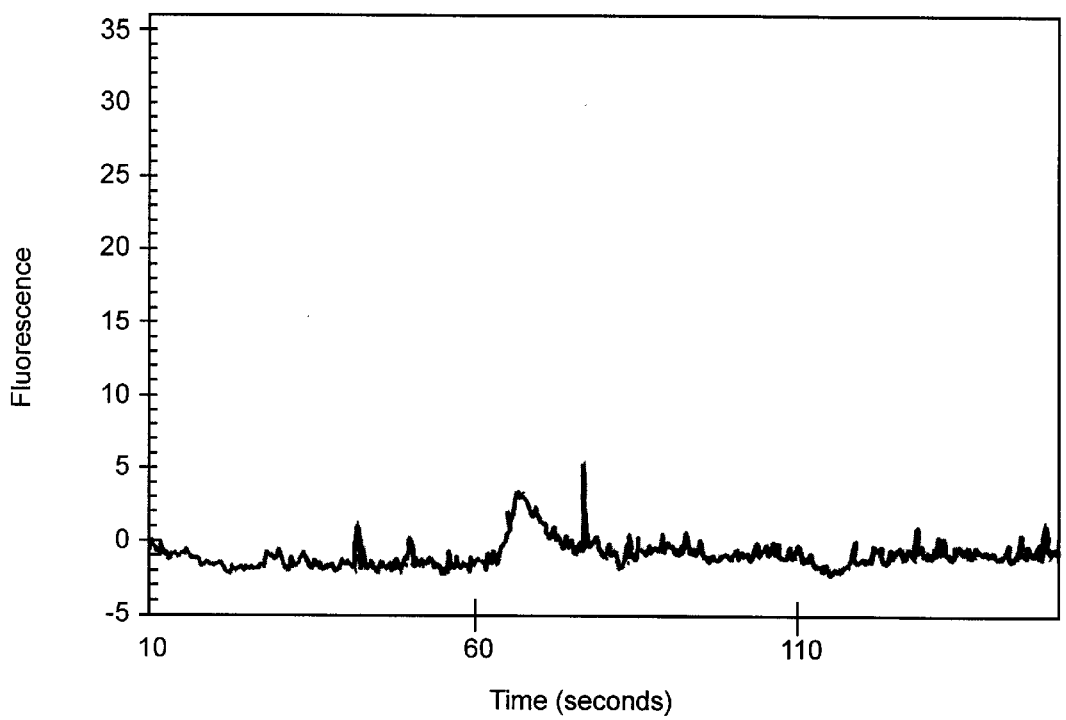
Figure 8D:
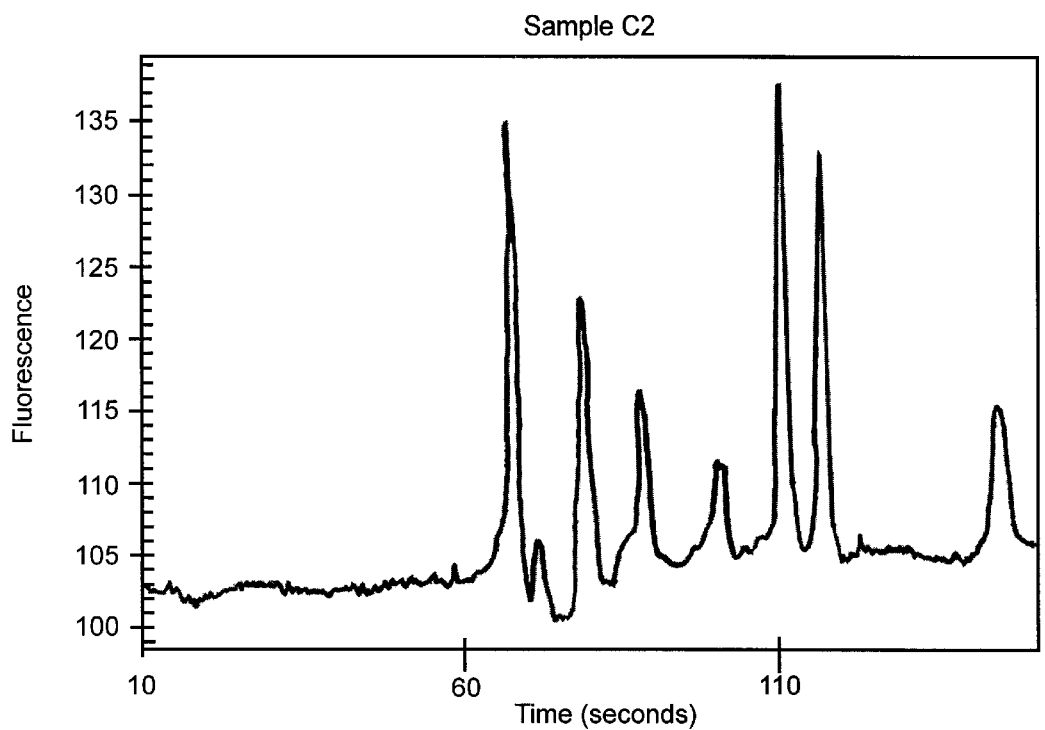

FIGS. 8A–8D illustrates plots of fluorescence versus time, as detected at the detection point 732 in a 2100 Bioanalyzer (Agilent Technologies, Inc.) for a standard separation performed without a post separation treatment and with a post separation dilution. Specifically, FIGS. 8A and B show a blank run (no polypeptides in the sample) and a protein sample run in a microfluidic device having no post separation dilution functionality. The device was functionally similar to the device channel layout shown in FIG. 1. As shown, the data from the blank and polypeptide runs included substantial background and other baseline problems including a large detergent dye front, followed by a baseline divot and a following dye hump. These same baseline deviations were found in the sample separation run, which cause substantial difficulty in qualifying and quantifying the separation data. FIGS. 8C and 8D illustrate the same blank run and polypeptide sample analysis using a post separation dilution step where the Tris Tricine buffer was introduced into the separation channel downstream of the majority of the separation, but upstream of the detection point. As shown, the post-separation dilution step substantially reduces overall background fluorescence relative to the detected sample components over the non-diluted samples, while also reducing the baseline humps and dips that are associated with micelle dye binding, e.g., as seen in FIGS. 8A and 8B.

Unless otherwise specifically noted, all concentration values provided herein refer to the concentration of a given component as that component was added to a mixture or solution independent of any conversion, dissociation, reaction of that component to a alter the component or transform that component into one or more different species once added to the mixture or solution.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of performing an analytical operation on a fluid first sample material, comprising:
   providing a microfluidic device that has a body having at least a first and a second channel disposed therein, the first channel comprising first and second channel segments, the first channel segment comprising a first fluid environment compatible with the performance of a first separation operation, the second channel segment comprising a detection zone for detecting the analytical operation wherein the second channel intersects the first channel at a first location substantially downstream along the first channel segment and immediately upsteam of the detection zone;
   flowing the first sample material through the first channel segment to perform the first separation operation;
   flowing the first sample material from the first channel segment into the second channel segment; and
   introducing a first diluent consisting essentially of buffer into the first channel at the first location from the second channel, the diluent producing a second fluid environment within the second channel segment of the first channel, the second environment being more compatible than the first environment for detecting a result of the separation operation.

2. The method of claim 1, wherein the separation operation comprises an electrophoretic polypeptide separation, and the first fluid environment comprises a detergent concentration that is at or above a critical micelle concentration (CMC) for the detergent.

3. The method of claim 2, wherein the first fluid environment comprises the detergent at a concentration of greater than about 0.1%.

4. The method of claim 2, wherein detecting the analytical operation comprises detection of a lipophilic dye associated with polypeptides separated in the first operation, and the second fluid environment comprises die detergent at a concentration that is below the CMC for the detergent.

5. The method of claim 4, wherein the second fluid environment comprises the detergent at a concentration of less than 0.1%.

6. The method of claim 4, wherein the second fluid environment comprises the detergent at a concentration of about 0.05%.

7. The method of claim 2, wherein the providing step further comprises providing a separation buffer in at least the first channel segment, the separation buffer comprising a polymer matrix, a buffering agent, a first detergent and a lipophilic dye.

8. The method of claim 7, wherein the polymer matrix comprises a no-crosslinked polymer solution.

9. The method of claim 8, wherein the non-crosslinked polymer solution comprises a linear dimethylacrylamide polymer solution.

10. The method of claim 9, wherein the linear polyacrylamide polymer is present in the separation buffer at a concentration of between about 0.1 and about 20% (w/v).

11. The method of claim 7, wherein the first detergent comprises an alkylsulfonate detergent.

12. The method of claim 7, wherein the first detergent is selected from sodium octadecylsulfate, sodium decylsulfate and sodium dodecyl sulfate (SDS).

13. The method of claim 7, wherein the first detergent comprises sodium dodecyl sulfate (SDS).

14. The method of claim 7, wherein the first detergent is present in the separation buffer in the first channel segment at a concentration greater than about 0.03%.

15. The method of claim 7, wherein the diluent comprises the buffering agent with no detergent.

16. The method of claim 7, wherein the buffering agent comprises Tris-Tricine.

17. The method of claim 7, wherein the buffering agent is present in the separation buffer in the first channel segment at a concentration of between about 10 mM and about 100 mM.

18. The method of claims 7, wherein the lipophilic dye is a fluorescent lipophilic dye.

19. The method of claim 7, wherein the lipophilic dye is present in the separation buffer in the first channel segment at a concentration of from about 0.1 $\mu$M to about 20 $\mu$M.

20. A device for separating polypeptides, comprising:
   a body structure having at least a first capillary channel disposed therein;
   a separation buffer disposed in the first capillary channel, the separation buffer comprising:
      a non-crosslinked polymer solution;
      a buffering agent;
      a first detergent; and
      a lipophilic dye capable of binding to the polypeptide or polypeptides; and
   a first port disposed in the body structure in fluid communication with the first capillary channel, for introducing polypeptides into the first capillary channel.

21. The device of claim 20, wherein the first port comprises a sample fluid disposed therein, the sample fluid comprising at least a first polypeptide of interest, and a second detergent at a concentration that is between about 0.05× and 3× a concentration of the first detergent in the separation buffer.

22. The device of claim 20, wherein the first port comprises a sample fluid disposed therein, the sample fluid comprising at least a first polypeptide of interest, and a second detergent at a concentration that is less than a concentration of the first detergent in the separation buffer.

23. The device of claim 20, wherein the first port comprises a sample fluid disposed therein, the sample fluid comprising at least a first polypeptide of interest, and a second detergent at a concentration that is between about 0.0025% and 1% (w/v).

24. The device of claim 20, wherein the first port comprises a sample fluid disposed therein, the sample fluid comprising at least a first polypeptide of interest, and a second detergent at a concentration that is between about 0.0025% and 0.5% (w/v).

25. The device of claim 20, wherein the first port comprises a sample fluid disposed therein, the sample fluid comprising at least a first polypeptide of interest, and a second detergent at a concentration that is less than about 0.5% (w/v).

26. The device of claim 20, wherein the body structure comprises a capillary element having the first capillary channel disposed therein, the first port comprising at least a first open end of the first capillary channel.

27. The device of claim 20, wherein the body structure comprises a planar substrate having the first capillary channel disposed in an interior portion thereof, the port being disposed in a surface of the body.

28. The device of claim 27, further comprising at least a second capillary channel disposed in the interior portion of the planar substrate, the second channel being in fluid communication with the first capillary channel.

29. The device of claim 28, wherein the second capillary channel intersects and crosses the first capillary channel.

30. The device of claim 28, wherein the first port is in fluid communication with the first capillary channel via the second capillary channel.

31. The device of claim 28, further comprising at least a second port disposed in the body structure and in fluid communication with the first capillary channel.

32. The device of claim 31, wherein each of the at least first and second ports are in fluid communication with the first capillary channel via the second capillary channel.

* * * * *

UNITED STATES PATENT AND TRADEMARK OFFICE
CERTIFICATE OF CORRECTION

PATENT NO.   : 6,475,364 B1  
DATED        : November 5, 2002  
INVENTOR(S)  : Dubrow et al.

Page 1 of 1

It is certified that error appears in the above-identified patent and that said Letters Patent is hereby corrected as shown below:

Column 20,  
Line 40, please delete "die" and insert -- the --.  
Line 54, please delete "no" and insert -- non --.

Column 21,  
Line 12, please delete "claims" and insert -- claim --.

Signed and Sealed this

Eighteenth Day of February, 2003

JAMES E. ROGAN  
*Director of the United States Patent and Trademark Office*